US00PP25074P3

(12) United States Plant Patent
Meadows, Jr.

(10) Patent No.: US PP25,074 P3
(45) Date of Patent: Nov. 18, 2014

(54) ***RHODODENDRON* PLANT NAMED 'ROBLEU'**

(50) Latin Name: ***Rhododendron* hybrid**
Varietal Denomination: ROBLEU

(71) Applicant: Thomas Dennis Meadows, Jr., Daphne, AL (US)

(72) Inventor: Thomas Dennis Meadows, Jr., Daphne, AL (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 13/694,813

(22) Filed: Jan. 7, 2013

(65) Prior Publication Data

US 2014/0196186 P1 Jul. 10, 2014

(51) Int. Cl.
*A01H 5/00* (2006.01)

(52) U.S. Cl.
USPC ..... Plt./240

(58) Field of Classification Search
USPC ..... Plt./240, 239
See application file for complete search history.

*Primary Examiner* — Anne Grunberg
(74) *Attorney, Agent, or Firm* — Cassandra Bright

(57) ABSTRACT

A new and distinct *Rhododendron* cultivar named 'ROBLEU' is disclosed, characterized by distinctive vibrant magenta flowers and unique flowering from Spring through Autumn. The new cultivar is a *Rhododendron,* suitable for ornamental garden purposes.

2 Drawing Sheets

Figure 1:
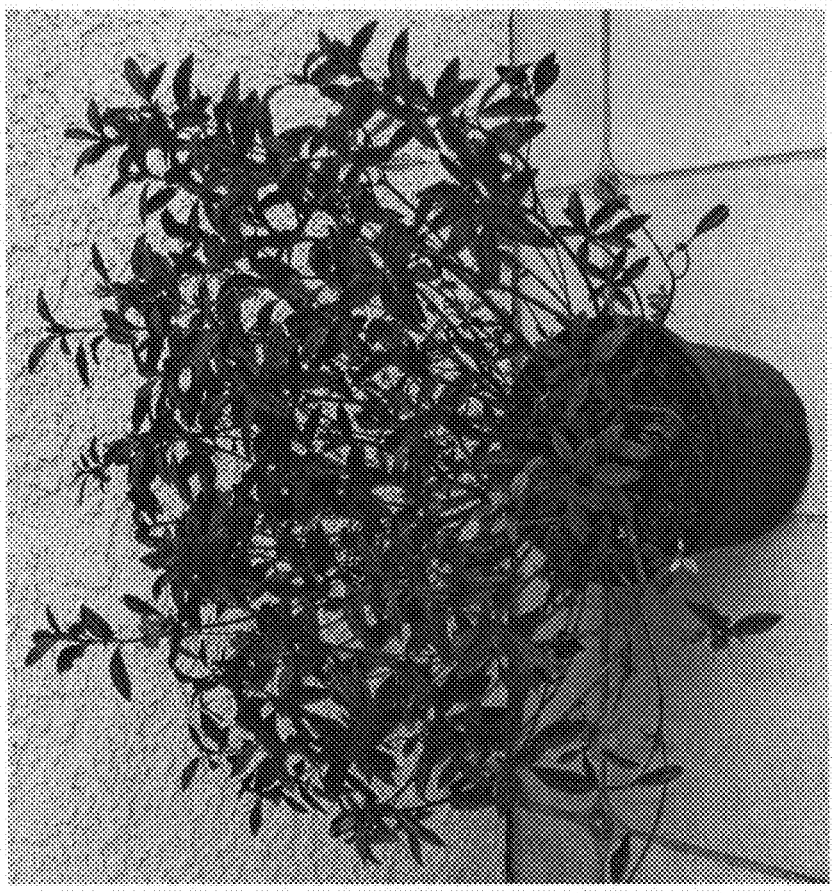

Latin name of the genus and species: *Rhododendron* hybrid.

Variety denomination: 'ROBLEU'.

BACKGROUND OF THE INVENTION

The new cultivar is a product of chance discovery by the inventor. This new variety, hereinafter referred to as 'ROBLEU', was discovered as a branch sport by Thomas Dennis Meadows Jr, Apr. 14, 2001 in Loxley, Ala., at a commercial nursery. The parent variety producing this naturally occurring mutation is *Rhododendron* 'Conlee' U.S. Plant Pat. No. 10,567.

After identifying the new variety as a potentially interesting selection, the inventor first organized propagation of 'ROBLEU' by vegetative cuttings on Jun. 12, 2001 at the same commercial nursery in Loxley, Ala. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'ROBLEU' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ROBLEU' These characteristics in combination distinguish 'ROBLEU' as a new and distinct *Rhododendron* cultivar:

1. The unique spring, summer, and fall blooming.
2. Vibrant magenta flowers
3. Easily propagated with semi-hardwood cuttings in late spring through the summer.
4. Good specimen plant.

5. Excellent performance in planters.
6. Very good foundation plant.
7. Does well as an understory plant in a woodland garden.
8. Hardy to Zone 7.
9. Attracts butterflies.
10. Attractive winter stem and foliage coloration.

COMPARISON TO PARENT VARIETY

'ROBLEU' is similar in most horticultural characteristics to the parent variety *Rhododendron* hybrid 'CONLEE' U.S. Plant Pat. No. 10,567. Plants of the new cultivar 'ROBLEU' however, produce flowers that are distinctively different in Red-Purple coloration, and significantly larger than flowers of the parent variety. Additionally, the mature plant height and spread of the new variety is less than that of the parent variety. Plant habit is overall more compact in the new variety, compared to the parent.

COMMERICAL COMPARISON

'ROBLEU' can be compared to the commercial variety *Rhododendron* hybrid 'Conlet', U.S. Plant Pat. No. 12,111. Plants of the new cultivar 'ROBLEU' are similar to plants of 'Conlet' in most horticultural characteristics, however, plants of the new cultivar 'ROBLEU' produce larger flowers, of a different Red-Purple coloration than those of 'Conlet'. Additionally, plants of 'ROBLEU' are larger than plants of 'Conlet'.

'ROBLEU' can also be compared to the commercial variety *Rhododendron* hybrid 'Conles' U.S. Plant Pat. No. 12,109. Plants of the new cultivar 'ROBLEU' are similar to plants of this comparator in most horticultural characteristics, however, plants of the new cultivar 'ROBLEU' produce larger flowers, of a different Red-Purple coloration than that of 'Conles'.

BRIEF DESCRIPTION OF THE PHOTOGRAPHS

The accompanying photograph in FIG. 1 illustrates in full color a typical plant of 'ROBLEU' grown outdoors in Alabama. The plant is approximately 2 years old, and is shown growing in a 3 gallon nursery container.

Figure 2:
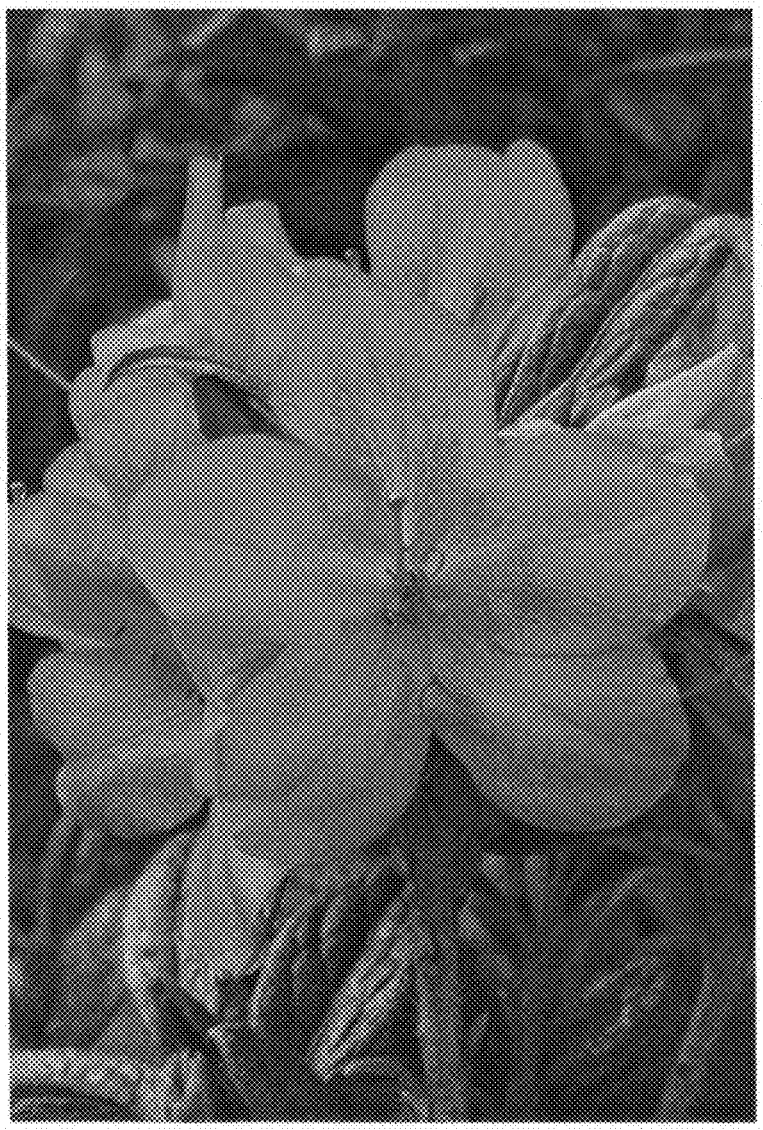

FIG. 2 illustrates in full color a close up of typical flowers of 'ROBLEU'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'ROBLEU' plants grown outdoors in Loxley, Ala. Plants are approximately 2 years old, in a 3 gallon nursery container. Measurements and numerical values represent averages of typical plant types.

Botanical classification: *Rhododendron* hybrid 'ROBLEU'.

PROPAGATION

Typically by semi-hardwood cuttings in spring and summer.

PLANT

Growth habit: Compact evergreen shrub. Slow to moderate growth rate.

Height: Approximately 66 cm to top of foliar and flowering plane.

Plant spread: Approximately 72 cm.

Branching characteristics: Moderately well branched, approximately 10 primary branches from center of plant, angled approximately 60° to 75° from center of plant. Each primary branches has 3 to 8 lateral branches.

Primary branches:

- *Length of primary branches*.—Approximately 24 to 32 cm.
- *Diameter of primary branches*.—Approximately 0.8 cm.
- *Primary branch strength*.—Very strong, difficult to break.
- *Primary branch color*.—Near RHS Yellow-Green 144B, with age, becoming covered with a thin bark like layer colored near Brown 200D.
- *Primary branch texture*.—Young growth covered in appressed hairs, less than 0.1 cm long. Older growth scaly, covered in appressed hairs approximately 0.1 cm long, colored near White 155D.

Lateral branches:

- *Number of lateral branches*.—Approximately 3 to 8 per primary branch.
- *Length of lateral branches*.—Approximately 12 to 18 cm.
- *Diameter of lateral branches*.—Average 0.4 cm.
- *Lateral branch strength*.—Very strong, flexible.
- *Lateral branch color*.—Near RHS Greyed-Orange 176B.
- *Lateral branch texture*.—Covered in moderately dense appressed hairs, colored near RHS Greyed-Orange 176D.

Internode length: Range between 1.4 to 4.2 cm.

Age of plant described: Approximately 2 years.

FOLIAGE

Leaf:

- *Type*.—Simple.
- *Arrangement*.—Alternate.
- *Average length*.—Approximately 5.9 cm.
- *Average width*.—Approximately 2.7 cm.
- *Shape of blade*.—Elliptic.
- *Apex*.—Acute.
- *Base*.—Attenuate.
- *Attachment*.—Stalked.
- *Margin*.—Entire.
- *Texture of top surface*.—Leathery, hirsute. Hairs less than 1 mm.
- *Texture of bottom surface*.—Mainly glabrous over surface, veins and margin hirsute.
- *Foliage scent*.—None.
- *Color*.—Young foliage upper side: Near RHS Green 137B. Young foliage under side: Near RHS Yellow-Green 144B. Mature foliage upper side: Near RHS Green 137A, but darker. Mature foliage under side: Near RHS Green 138B.
- *Venation*.—Type: Pinnate. Venation color upper side: Near RHS Yellow-Green 144A. Venation color under side: Near RHS Yellow-Green N144D.
- *Petiole*.—Length: About 1.0 cm. Diameter: About 0.25 cm. Color: Near RHS Yellow-Green N144C, upper and lower surfaces.

FLOWER

Bloom period: Plants begin flowering in the Spring, around late March, and continue to produce flowers throughout Summer and Fall. Flowering ends with frost, typically October or November.

Flower:

- *Arrangement*.—Axillary clusters of single, perfect, open funnel shaped individual flowers. Typically 4 to 6 flowers per cluster.

Inflorescence:

- *Height*.—Average 9.0 cm.
- *Diameter*.—Average 8.8 cm.

Peduncle: No peduncle, clusters arise directly from axils.

Pedicel:

- *Length*.—Average 1.3 cm.
- *Diameter*.—0.25 cm.
- *Color*.—Near RHS Red 53B.
- *Texture*.—Densely pubescent.
- *Aspect*.—Straight to very slightly curved. Angle of attachment, approximately 45° angle from axil.

Flowers:

- *Length*.—Average 3.0 cm.
- *Diameter*.—Average 5.0 cm.
- *Facing direction*.—Outwardly and upwardly facing.
- *Persistent or self-cleaning*.—Petals self cleaning.
- *Fragrance*.—None.

Tube:

- *Tube length*.—Approximately 1.4 cm.
- *Tube width a widest point*.—Approximately 0.8 cm.
- *Tube width and narrowest point*.—Approximately 0.4 cm.

Petals:

- *Unfused petal segments*.—Length: Approximately 1.9 cm. Width: Approximately 1.8 cm.

*Apex.*—Retuse.
*Shape of petal.*—Unfused portion, obovate.
*Petal margin.*—Entire to infrequent crenations. Ruffled aspect along margin.
*Petal arrangement.*—Approximately ¼ fused from base.
*Petal number.*—5.
*Petal texture.*—Smooth.
*Color.*—Inner surface at first opening: Near RHS Red-Purple 63B. Irregular small dots and stripes near Red-Purple 61A occasionally occur across petal surface of 1 to 3 petals per flowers. Outer surface at first opening: Near RHS Red-Purple 64B. Inner surface at maturity: Near RHS Red-Purple N57C. Irregular small dots and stripes near Red-Purple 64A occasionally occur across petal surface of 1 to 3 petals per flowers. Outer surface at maturity: Near RHS Red-Purple 64C. Upper surface at fading: Near RHS Red-Purple 63A. Irregular small dots and stripes near Red-Purple 64A occasionally occur across petal surface of 1 to 3 petals per flowers. Under surface at fading: Near RHS Red-Purple 63B.

Bud:
*Shape.*—Elliptic.
*Length.*—2.5 cm.
*Diameter.*—0.9 cm.
*Color.*—Near RHS Red-Purple 64B.

Calyx/sepals:
*Quantity per flower.*—5 sepals.
*Shape.*—Narrow deltate.
*Length.*—0.5 cm.
*Width.*—0.3 cm.
*Apex.*—Acute.
*Base.*—Fused.
*Margin.*—Entire.
*Texture.*—Highly pubescent
*Color.*—Inner Surface: Near RHS Yellow-Green 145A. Outer Surface: Near RHS Yellow-Green 145B.

REPRODUCTIVE ORGANS

Stamens:
*Number.*—10.
*Length.*—2.5 cm.
*Width.*—0.1 cm.
*Color.*—Near RHS Red-Purple 64C.
*Anthers.*—Length: Approximately 0.3 cm. Color: Near RHS Greyed-Purple 187A. Pollen: Not observed to date.

Pistil:
*Number.*—1.
*Length.*—5.4 cm.
*Style.*—Length: 4.9 cm. Color: Near RHS Red-Purple N57A.
*Stigma.*—Globular, colored near Red-Purple 59A.
*Ovary.*—Sericeous texture. Approximately 0.2 cm in diameter. Colored near Yellow-Green 145A. Hairs colored near White N155D.

OTHER CHARACTERISTICS

Disease and pest resistance: Not observed to be susceptible nor resistant to normal diseases and pests of *Rhododendron.*
Temperature tolerance: USDA Zone 7.
Fruit/seed production: Not observed to date.

What is claimed is:

1. A new and distinct cultivar of *Rhododendron* plant named 'ROBLEU' as herein illustrated and described.

* * * * *